(12) United States Patent
Du et al.

(10) Patent No.: US 12,213,784 B2
(45) Date of Patent: Feb. 4, 2025

(54) DURABLE ENZYME-BASED BIOSENSOR AND PROCESS FOR DROP DEPOSITION IMMOBILIZATION

(71) Applicant: Northeastern University, Boston, MA (US)

(72) Inventors: Yunqing Du, Quincy, MA (US); Ming L. Wang, Ipswich, MA (US)

(73) Assignee: Northeastern University, Boston, MA (US)

( * ) Notice: Subject to any disclaimer, the term of this patent is extended or adjusted under 35 U.S.C. 154(b) by 1050 days.

(21) Appl. No.: 16/468,146

(22) PCT Filed: Dec. 11, 2017

(86) PCT No.: PCT/US2017/065624
§ 371 (c)(1),
(2) Date: Jun. 10, 2019

(87) PCT Pub. No.: WO2018/107168
PCT Pub. Date: Jun. 14, 2018

(65) Prior Publication Data
US 2020/0405200 A1  Dec. 31, 2020

Related U.S. Application Data

(60) Provisional application No. 62/432,513, filed on Dec. 9, 2016.

(51) Int. Cl.
*A61B 5/1486* (2006.01)
*A61B 5/145* (2006.01)
*G01N 27/327* (2006.01)

(52) U.S. Cl.
CPC ........ *A61B 5/1486* (2013.01); *A61B 5/14532* (2013.01); *G01N 27/3271* (2013.01); *A61B 2562/0285* (2013.01)

(58) Field of Classification Search
CPC .............. A61B 5/1486; A61B 5/14532; G01N 27/3271
See application file for complete search history.

(56) References Cited

U.S. PATENT DOCUMENTS 5,116,729 A    5/1992  Ismail et al.
2007/0042496 A1*  2/2007  Okamoto ................ H01J 49/40
                                                          702/19

(Continued)

FOREIGN PATENT DOCUMENTS

CN       1815236 A      8/2006
CN     101393159 A      3/2009

(Continued)

OTHER PUBLICATIONS

Du et al., "Sensing of Salivary Glucose Using Nano-Structured Biosensors". Biosensors 2016, 6(1): p. 10; Journal of Diabetes Science and Technology, pp. 1344-1352.

(Continued)

*Primary Examiner* — David J. McCrosky
*Assistant Examiner* — Meghan R Kumar
(74) *Attorney, Agent, or Firm* — Verrill Dana, LLP

(57) ABSTRACT

A sensor having improved shelf life is provided for determining concentration of a biomarker in a liquid sample. The sensor functions by electrochemical detection and requires use of a biomolecule, e.g., an enzyme that catalyzes an electron transfer reaction specific for the biomarker. The sensor requires use of a quaternary ammonium compound as a bio-linker. It further requires crosslinking of the biomolecule for improved stability.

23 Claims, 3 Drawing Sheets

(56) References Cited

U.S. PATENT DOCUMENTS

| | | | |
|---|---|---|---|
| 2010/0009456 A1 | 1/2010 | Prins et al. | |
| 2011/0236951 A1* | 9/2011 | Grate | C12N 11/089 |
| | | | 527/200 |
| 2011/0263011 A1 | 10/2011 | Qiu et al. | |
| 2012/0216936 A1 | 8/2012 | Forrow et al. | |
| 2012/0228149 A1* | 9/2012 | Boal | C25B 11/02 |
| | | | 204/278.5 |
| 2012/0325679 A1* | 12/2012 | Forrow | C12Q 1/004 |
| | | | 205/777.5 |
| 2013/0324820 A1* | 12/2013 | Petillo | A61B 5/14865 |
| | | | 205/109 |
| 2014/0197042 A1* | 7/2014 | Zhang | G01N 27/3273 |
| | | | 427/2.12 |

FOREIGN PATENT DOCUMENTS

| | | |
|---|---|---|
| CN | 103175884 A | 6/2013 |
| CN | 10502972 A | 11/2015 |
| CN | 105708416 A | 6/2016 |
| EP | 1688742 A1 | 8/2006 |
| WO | 2003035891 A2 | 5/2003 |

OTHER PUBLICATIONS

Gibson, T. D., "Biosensors: The Stability Problem", Analusis, 1999, 27(7): p. 630-638.

Double-Do Protein Cross-Linkers, Handbook & Selection Guide, Archived, Dec. 7, 2017; Retrieved from www.GBiosciences.com.

Castagnola et al., "Potential applications of human saliva as diagnostic fluid", Acta Otorhinolaryngologica Italica, 2011; 31:347-357.

Zhang et al., "On-chip highly sensitive saliva glucose sensing using multilayer films composed of single-walled carbon hanotubes, gold nanoparticles, and glucose oxidase", Sensing and Bio-Sensing Research, vol. 4, Jun. 2015, pp. 96-102.

Malon et al., "Saliva-Based Biosensors: Noninvasive Monitoring Tool for Clinical Diagnostics", BioMed Research International, vol. 2014, Article ID 962903, 20 pages, 2014.

Lichter et al., "Design of Antibacterial Surfaces and Interfaces: Polyelectrolyte Multilayers as a Multifunctional Platform", Macromolecules, 2009, 42(22), pp. 8573-8586.

Petkova et al., "Gold and silver nanoparticles for biomolecule immobilization and enzymatic catalysis", Nanoscale Research Letters, 2012, 7, Article No. 287, 10 pages.

Moore et al., "Improving the Environment for Immobilized Dehydrogenase Enzymes by Modifying Nafion with Tetraalkylammonium Bromides", Biomacromolecules 2004, 5(4), pp. 1241-1247.

Meredith et al., "Hydrophobic Salt-modified Nafion for Enzyme Immobilization and Stabilization", Jove-Journal of Visualized Experiments, 2012 (65), 5 pages.

Zhou et al., "Immunoassays for cortisol using antibody-doped sol-gel silica", Journal of Materials Chemistry, 2004, 12 (14): p. 2311-2316.

Zucca and Sanjust, "Inorganic Materials as Supports for Covalent Enzyme Immobilization: Methods and Mechanisms", Methods and Mechanisms. Molecules, 2014, 19(9): p. 14139-14194.

Wong, "Salivary diagnostics powered by nanotechnologies, proteomics and genomics", J Am Dent Assoc, 2006, 137 (3): p. 313-21.

Wang et al., "A novel glucose biosensor based on the immobilization of glucose oxidase onto gold nanoparticles-modified Pb nanowires", Biosensors and Bioelectronics 25 (2009) 142-146.

* cited by examiner

DURABLE ENZYME-BASED BIOSENSOR AND PROCESS FOR DROP DEPOSITION IMMOBILIZATION

CROSS-REFERENCE TO RELATED APPLICATIONS

This application claims the priority of U.S. Provisional Application No. 62/432,513 filed Dec. 9, 2016, entitled "Durable Enzyme-Based Biosensors Platform Enabled by a Drop Deposition Immobilization Process", which is hereby incorporated by reference in its entirety.

BACKGROUND

A successful health care system provides better health to more people at lower cost on a continuous basis. Real-time point-of-care (POC) testing can assist in effective disease control and appropriate therapeutic interventions. In this regard, efforts are ongoing to develop noninvasive methods using saliva as an indicative fluid to screen patients for cancers. Wong, *J Calif Dent Assoc,* 2006, 2006. 34(4): p. 303-8; Wong, *J Am Dent Assoc,* 2006, 137(3): p. 313-21; and Castagnola, et al., *Acta Otorhinolaryngologica Italica,* 2011, 31(6): p. 347-357. In the area of chronic disease management, biomarker monitoring technology has been developed to provide patients a simple and fast way of measuring real-time health conditions with no pain, no risk of infection, and no-scarring, all of which make the process stress-free. The biosensors that have been developed toward this objective combine biological molecules with electrochemical detection to measure analyte(s) that include small molecules, proteins, hormones, and antigens. Zhang W, *Sensing and Biosensing Research,* 2015, 4: p. 96-102; Du Y, *Biosensors,* 2016, 6(1): p. 10; Du, *Journal of Diabetes Science and Technology,* 2016, 10(6): 1344-1352; Zhang W, *Sensing and Biosensing Research,* 2015, 4: p. 23-29; and Malon, et al., *Biomed Res Int,* vol. 2014, Article ID 962903. However, many of these biosensors, which use enzymes for detection of the analyte, have a short shelf life. This limits their use as reliable disease detection/monitoring devices.

There is a need for robust devices capable of real-time assessment of personal health and/or diagnosis of disease.

SUMMARY

The present technology provides robust and stable biosensors based on an electrochemical device containing a cross-linked biomolecule, such as an enzyme. The working electrode of the device is provided with a layer of nanomaterial sensor elements coated with a functionalization coating that contains the biomolecule. The biosensor is highly sensitive and capable of specific detection and quantification of an analyte or biomarker in a liquid sample. The biosensor typically has a shelf stability of one year or more.

One aspect of the present technology is a sensor for determining a concentration of a biomarker in a liquid sample. The sensor includes: an insulating or semiconducting substrate; at least one working electrode, a counter electrode, and a reference electrode, and a sample placement area on a surface of the substrate for containing the liquid sample during a determination of the biomarker concentration in the liquid sample. Each of the working electrode(s), counter electrode, and reference electrode includes a conductive metal layer deposited on the substrate in the sample placement area. The working electrode is coated in the sample placement area with a plurality of sensor elements. The sensor elements are functionalized with a functionalization coating comprising a quaternary ammonium compound, a plurality of metal nanoparticles, a crosslinked enzyme that catalyzes an electron transfer reaction specific for the biomarker. The working electrode, counter electrode, and reference electrode are connected to an amperometry circuit. The sensor measures electron transfer into the working electrode. An output voltage of the amperometry circuit correlates with concentration of the biomarker in the liquid sample deposited in the sample placement area.

Another aspect of the present technology is a method of determining a concentration of a biomarker in a liquid sample. The method includes the steps of: (a) providing the sensor described above; (b) introducing a liquid sample into the sample placement area of the sensor; and (c) determining the concentration in the liquid sample from an electrical output of the sensor.

Yet another aspect of the present technology is a biomarker analysis system containing the sensor described above and a signal conditioning and/or analysis device that processes an electrical signal from the sensor.

Still another aspect of the present technology is a biomarker sensor array comprising a plurality of sensors as described above sharing a common substrate.

Another aspect of the present technology is a method of fabricating a biomarker sensor. The method includes the steps of: (a) microfabricating one or more working electrodes, a reference electrode, and a counter electrode on the surface of an insulating substrate, wherein each of said electrodes contacts a sample placement area on the substrate; (b) depositing a plurality of sensor elements onto the working electrode; (c) depositing a functionalization coating onto the sensor elements, the functionalization coating comprising one or more functionalization layers; wherein each functionalization layer comprises a quaternary ammonium compound, a plurality of metal nanoparticles, an enzyme that catalyzes an electron transfer reaction specific for the biomarker; and (d) crosslinking the enzyme by applying a crosslinking reagent to the functionalization coating.

Still another aspect of the present technology is a kit containing the sensor described above provided in a vacuum storage container, such as a vacuum gel box.

The technology can be further summarized by the following list of embodiments.

1. A sensor for determining a concentration of a biomarker in a liquid sample, the sensor comprising:
   an insulating or semiconducting substrate;
   at least one working electrode, a counter electrode, and a reference electrode, and
   a sample placement area on a surface of the substrate for containing the liquid sample during a determination of the biomarker concentration in the liquid sample;
   wherein each of the working electrode(s), counter electrode, and reference electrode comprises a conductive metal layer deposited on the substrate in the sample placement area;
   wherein the working electrode is coated in the sample placement area with a plurality of sensor elements;
   wherein the sensor elements are functionalized with a functionalization coating comprising a quaternary ammonium compound, a plurality of metal nanoparticles, a crosslinked enzyme that catalyzes an electron transfer reaction specific for the biomarker;
   wherein the working electrode, counter electrode, and reference electrode are connected to an amperometry circuit;

wherein the sensor measures electron transfer into the working electrode; and wherein an output voltage of the amperometry circuit correlates with concentration of the biomarker in the liquid sample deposited in the sample placement area.

2. The sensor of embodiment 1, wherein the substrate comprises a material selected from the group consisting of silicon, glass, paper, alumina, ceramic, a non-conductive polymer, and combinations thereof.

3. The sensor of embodiment 1 or 2, wherein the working electrode comprises one or more materials selected from the group consisting of gold, platinum, graphite, carbon, iridium, silver, silver/silver chloride, copper, bismuth, titanium, antimony, chromium, nickel, tin, aluminum, molybdenum, lead, tanatalum, tungsten, steel, and combinations thereof.

4. The sensor of any of the preceding embodiments, wherein the sensor elements comprise a material selected from the group consisting of single-walled carbon nanotubes (SWNT), double-walled carbon nanotubes, multi-walled carbon nanotubes, graphite, graphene, carbon nanofibers, carbon nanowires, carbon nanorods, and combinations thereof.

5. The sensor of any of the preceding embodiments, wherein the functionalization coating does not contain a polycationic polymer.

6. The sensor of any of the preceding embodiments, wherein the quaternary ammonium compound comprises alkyl chains having a chain length from about $C_2$ to about $C_{16}$.

7. The sensor of any of the preceding embodiments, wherein the quaternary ammonium compound is a chloride or bromide salt.

8. The sensor of any of the preceding embodiments, wherein the quaternary ammonium compound is selected from the group consisting of tetraethylammonium bromide, tetrapropylammonium bromide, tetrabutylammonium bromide, hexadecyltrimethylammonium bromide, benzalkonium chloride, alkyldimethylbenzylammonium chloride having alkyl chain lengths from $C_{12}$ to $C_{16}$, and dialkyldimethylammonium chloride having alkyl chain lengths from $C_8$ to $C_{10}$.

9. The sensor of any of the preceding embodiments, wherein the plurality of metal nanoparticles are selected from the group consisting of gold nanoparticles, platinum nanoparticles, silver nanoparticles, copper nanoparticles, palladium nanoparticles, ruthenium nanoparticles, rhenium nanoparticles, and combinations thereof.

10. The sensor of any of the preceding embodiments, wherein the enzyme is crosslinked using a homobifunctional or heterobifunctional crosslinking reagent.

11. The sensor of any of the preceding embodiments, wherein the enzyme is crosslinked by a reagent selected from the group consisting of glutaraldehyde, 1-ethyl-3-(3-dimethylaminopropyl)carbodiimide, N-hydroxysuccinimide, N-hydroxysulfosuccinimide, dicyclohexylcarbodiimide, dimethyl adipimidate, dimethyl suberimidate, and combinations thereof.

12. The sensor of any of the preceding embodiments, further comprising a protective membrane covering the functionalized sensor elements.

13. The sensor of any of the preceding embodiments, wherein the protective membrane comprises Nafion, poly (diallyl dimethylammonium) chloride, eggshell membrane, hydrogel, bovine serum albumin, a lipid bilayer.

14. The sensor of any of the preceding embodiments having a shelf life of at least about nine months.

15. The sensor of any of the preceding embodiments having a shelf life of at least about one year.

16. The sensor of any of the preceding embodiments, configured as a disposable device or a reusable device.

17. The sensor of any of the preceding embodiments, wherein the enzyme is glucose oxidase and the biomarker is glucose.

18. The sensor of embodiment 17 that is capable of detecting glucose at concentrations down to 5 $\mu$M.

19. The sensor of embodiment 17 or 18 that has a response time of 30 seconds or less.

20. The sensor of any of embodiments 17-19 that has a sensitivity of at least 4.8 mA·s/M.

21. The sensor of any of embodiments 17-20 that is configured for determination of glucose concentration in saliva.

22. A method of determining a concentration of a biomarker in a liquid sample, the method comprising the steps of:
   (a) providing the sensor of any of embodiments 1-21;
   (b) introducing a liquid sample into the sample placement area of the sensor; and
   (c) determining the concentration in the liquid sample from an electrical output of the sensor.

23. The method of embodiment 22 further comprising the steps of:
   (d) removing the liquid sample introduced in step (b);
   (e) introducing a new liquid sample into the sample placement area of the sensor; and
   (f) determining a new biomarker concentration in the new liquid sample from an electrical output of the sensor.

24. The method of embodiment 22 or 23, wherein the enzyme is glucose oxidase, the biomarker measured is glucose, and liquid sample is from a subject who has diabetes, is suspected of having diabetes, or is healthy.

25. The method of any of embodiments 22-24, wherein the liquid sample is saliva.

26. A biomarker analysis system comprising:
   the sensor of any of embodiments 1-21;
   a signal conditioning and/or analysis device that processes an electrical signal from the sensor.

27. The biomarker analysis system of embodiment 26, further comprising a transmitter device for sending a radio signal to a remote receiver and/or to a data processing device, wherein the radio signal carries information related to a biomarker concentration in the liquid sample, the information obtained from the signal conditioning and/or analysis device.

28. The biomarker analysis system of embodiment 26 or 27, further comprising a memory device for accumulating data related to the biomarker concentration in the liquid sample, the data obtained at different times or from different liquid samples.

29. The biomarker analysis system of any of embodiments 26-28, further comprising a device for chemically or physically processing a liquid sample and delivering the processed sample to the sample placement area of the device.

30. A biomarker sensor array comprising a plurality of sensors according to any of embodiments 1-21 sharing a common substrate.

31. A method of fabricating a biomarker sensor, comprising the steps of:
   (a) microfabricating one or more working electrodes, a reference electrode, and a counter electrode on the surface of an insulating substrate, wherein each of said electrodes contacts a sample placement area on the substrate;
   (b) depositing a plurality of sensor elements onto the working electrode;

(c) depositing a functionalization coating onto the sensor elements, the functionalization coating comprising one or more functionalization layers; wherein each functionalization layer comprises a quaternary ammonium compound, a plurality of metal nanoparticles, an enzyme that catalyzes an electron transfer reaction specific for the biomarker; and (d) crosslinking the enzyme by applying a crosslinking reagent to the functionalization coating.

32. The method of embodiment 31, wherein the crosslinking reagent is applied to the top of the functionalization coating, or wherein the crosslinking reagent is applying by its inclusion in one or more of the one or more functionalization layers.

33. The method of embodiment 31 or 32, wherein the one or more functionalization layers are deposited by depositing sublayers through drop deposition of solutions or suspensions comprising the quaternary ammonium compound, the metal nanoparticles, and the enzyme.

34. The method of embodiment 31 or 32, wherein the one or more functionalization layers are deposited through drop deposition of a single suspension comprising the quaternary ammonium compound, the metal nanoparticles, and the enzyme.

35. The method of any of embodiments 31-34, wherein the single suspension further comprises a homobifunctional or heterobifunctional crosslinking reagent.

36. The method of any of embodiments 31-35, wherein the enzyme is crosslinked by a reagent selected from the group consisting of glutaraldehyde, 1-ethyl-3-(3-dimethylaminopropyl)carbodiimide, N-hydroxysuccinimide, N-hydroxysulfosuccinimide, dicyclohexylcarbodiimide, dimethyl adipimidate, dimethyl suberimidate, and combinations thereof.

37. The method of any of embodiments 31-36, further comprising depositing a sensor element protective membrane over the functionalization layers.

38. The method of any of embodiments 31-37, wherein the sensor elements are deposited onto the working electrode by a self-assembly process comprising depositing a liquid suspension of sensor elements onto the electrode.

39. A kit comprising the sensor of any of embodiment 1-21 or the biomarker analysis system of any of embodiments 26-29 or the biomarker sensor array of embodiment 30 in a vacuum storage container.

DETAILED DESCRIPTION

Figure 1:
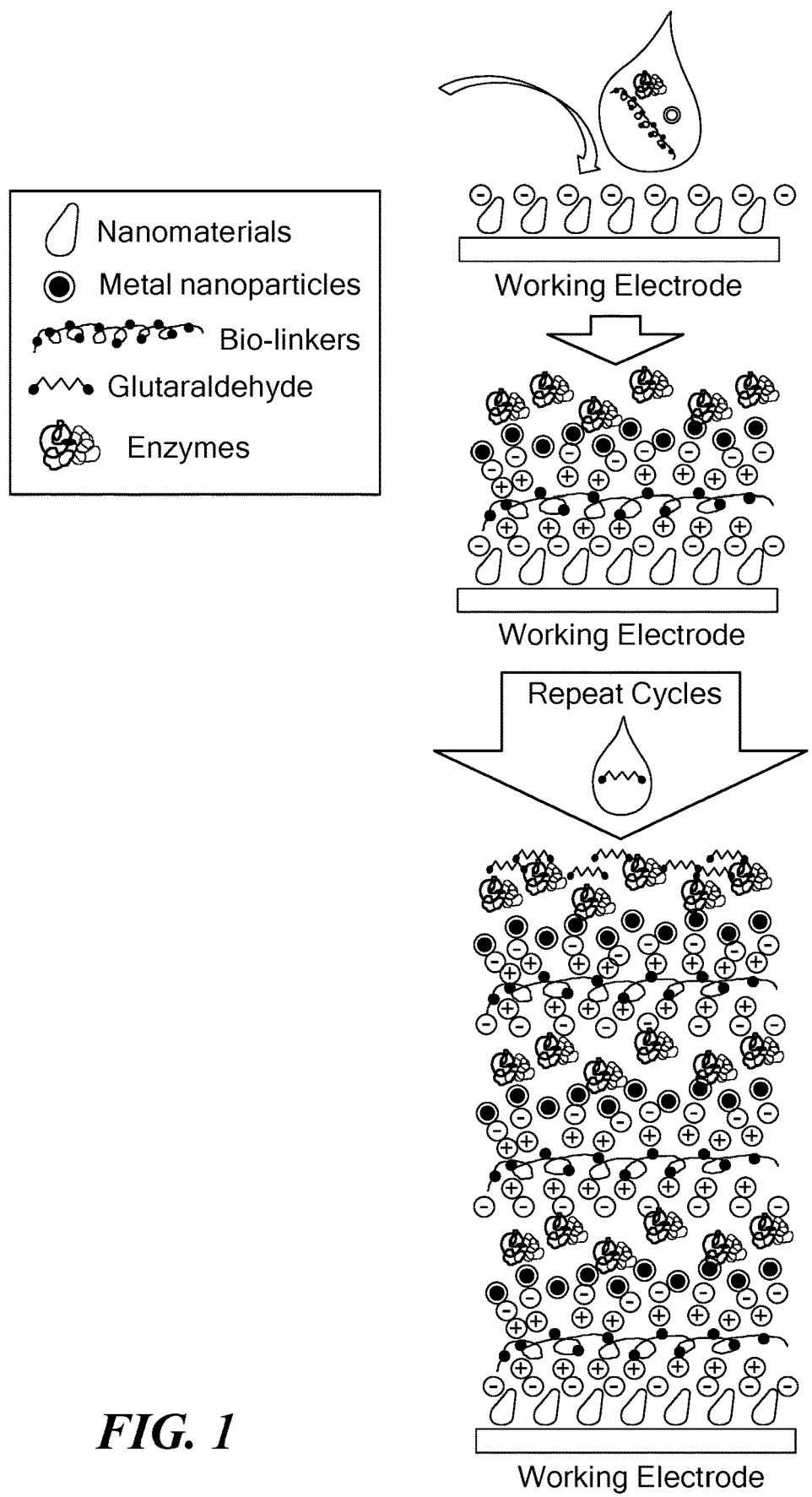
FIG. 1 depicts fabrication of an exemplary enzyme-based biosensor according to the present technology. The fabrication process includes depositing a layer of sensor elements (i.e., a plurality of nanoelements such as single walled carbon nanotubes (SWNT)) onto a working electrode followed by repeated cycles of deposition of a suspension containing components essential for functionalization of the sensor elements and the electrode. The biosensor is stabilized by a bio-linker and a cross-linker.
Figure 2A:
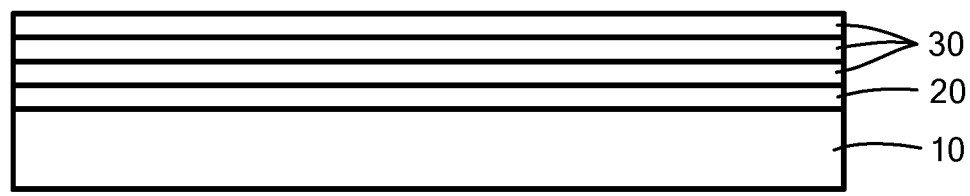
FIG. 2A is a schematic diagram of an embodiment of a functionalized electrode showing an electrode 10 coated with a sensor element layer 20 and multiple functionalization layers 30 deposited over the sensor element layer.
Figure 2B:
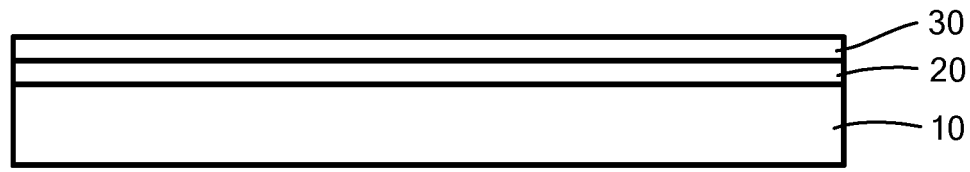
FIG. 2B shows another embodiment of a functionalized electrode that has a single functionalization layer 30 deposited onto the sensor elements 20.

The technology described herein is directed to detection of biomarkers using a biomolecule-based biosensor having increased shelf life compared to previous biosensors. In a preferred embodiment, the biosensor relies on the use of an enzyme that catalyzes an electron transfer reaction specific for the biomarker to be detected. In other embodiments, a biomarker is detected using a biomolecule other than an enzyme, such as non-enzyme proteins, antibodies, aptamers, lipids, nucleotides, bacteria, and combinations thereof.

Previous enzyme-based biosensors, such as those using glucose oxidase, generally suffer from having a short shelf life, often less than a month, or lasting only a few days, largely because the enzymes used in their design are labile. This limits the clinical use of enzyme-based biosensors. See Gibson, T. D. Biosensors: The Stability Problem, *Analusis*, 1999, 27(7): p. 630-638. This disadvantage is overcome by the biosensors made according to the present technology. This technology requires (i) crosslinking of the enzyme (or other biomolecule) to enhance stability, and (ii) the use of quaternary ammonium compounds to enhance shelf life and improve sensitivity.

As used herein, "shelf life" refers to a period of time during which generally less than 50%, such as less than 30%, less than 20%, less than 10%, less than 5%, less than 2%, or less than 1% of the initial activity, such as sensitivity (lower limit of detection of an analyte), responsiveness (i.e., voltage output for a given analyte concentration), or signal-to-noise ratio is lost. Shelf life can be measured and specified as a function of storage conditions, such as at room temperature, at refrigerator temperature (about 4° C.), at freezer temperature, under vacuum, or under ambient conditions (room temperature and atmospheric pressure). Generally, shelf life is specified at room temperature and under vacuum.

The biosensors described herein can include, for example, a three- or four-electrode electrochemical cell on a substrate or a chip. Preferably, each biosensor contains three electrodes: a working electrode, a counter electrode, and a reference electrode. An enzyme is attached to a component deposited on the working electrode. A sample liquid containing the analyte of interest, e.g. glucose, when dropped onto the sensor, touches all three electrodes. The amount of analyte present is measured using an amperometric method. The geometry and the relative areas of the electrodes are preferably optimized to yield the best results for the volume of the sample used for the test. The sample volume can be in the range of a few nanoliters to several milliliters or more.

In order to construct the biosensor, the working electrode is coated with a layer of a nanomaterial such as single wall carbon nanotubes (SWNT) or other nanoelements, which are usually conducting or semiconducting. A suitable process is described in WO 2014/110,492, which is incorporated herein by reference herein in its entirety. The layer of nanoelements is referred to herein as the "sensor elements" because these nanoelements provide a conductive, high surface area contact for the biomolecule sensors of the device. Next, a functionalization coating is formed over the sensor elements. The functionalization layer or layers can be added either by a layer-by-layer assembly process or by drop deposition of a single layer containing all of the required components of the functionalization coating. Components of the functionalization layers include a "bio-linker" such as a quaternary ammonium compound, metal nanoparticles, and an enzyme (or other biomolecule), which is preferably adsorbed to the metal nanoparticles. A crosslinking reagent is added to each layer, or only to the uppermost layer or top surface of the coating, after addition of the enzyme, and cross-links the enzyme within the functionalization coating. If the crosslinker is added as the last sublayer, it can penetrate through the underlying layers and bring about crosslinking of the enzyme (or the other biomolecule) in those layers. See FIG. 1.

Preferably, in the present technology, the use of polyallylamine (PAA), chitosan, and other cationic polymers as an electrode coating or within the functionalization coating is avoided.

The bio-linkers used in the assembly of multi-layer films are preferably quaternary ammonium compounds. In general, these compounds are known to serve as antimicrobials (Jenny A. L, *Macromolecules,* 2009, 42(22): p. 8573-8586; Lichter, et al., *Macromolecules,* 2009, 42: p. 8573-86.), nanoparticles stabilizers (Petkova, et al., *Nanoscale Research Letters,* 2012, 7(1):287), Nafion modifiers (Moore, et al., *Biomacromolecules,* 2004, 5(4): p. 1241-1247; Meredith, et al., *Jove-Journal of Visualized Experiments,* 2012 (65)), or cationic surfactants (Zhou, et al., *Journal of Materials Chemistry,* 2004, 14(14): p. 2311-2316). In the biosensor described herein, they result in enhanced shelf life and improved sensitivity.

The present technology requires crosslinking of the enzyme (or another biomolecule) whose activity is relied upon for the functioning of the biosensor. Protein crosslinking has been used for many purposes including studying protein structure and function, anchoring proteins to solid supports, preparation of immunogens, immunotoxins, and other conjugated protein reagents, and for stabilizing protein tertiary and quaternary structure. In the present technology, crosslinking is used to stabilize the structure of a protein such that the biosensor has a prolonged shelf life. Several methods of crosslinking proteins are known (see Double-Do Protein Cross-Linkers, Handbook & Selection Guide, Archived, Dec. 7, 2017; and Thermo Scientific Crosslinking Technical Handbook, Archived, Dec. 7, 2017). Among the functional groups that can be targeted with cross-linking agents are primary amines, carboxyls, sulfhydryls, carbohydrates and carboxylic acids. Protein molecules have many of these functional groups and therefore can be readily conjugated using cross-linking agents. Care must be taken to optimize the degree of crosslinking. Too little, and the shelf life of the sensor might be reduced; too much, and the enzyme or other biomolecule can be denatured and lose its activity and/or specificity.

Crosslinking agents can be divided into two groups based on the number and similarity of their reactive groups: homobifunctional crosslinking agents having two reactive ends that are identical, and heterobifunctional crosslinking agents having two different reactive moieties. Homobifunctional cross-linkers are used in one step reactions whereas heterobifunctional cross-linkers require two sequential reactions. The former affords ease of use and the latter greater control over the crosslinking process. A preferred crosslinking reagent is glutaraldehyde (see FIG. 1) or a glutaraldehyde polymer, which is a homobifunctional crosslinking agent. 1-Ethyl-3-(3-dimethylaminopropyl) carbodiimide hydrochloride, dicyclohexylcarbodiimide, dimethyl adipimidate, and dimethyl suberimidate are examples of other reagents that can be used.

Enzyme crosslinking, combined with the drop coating deposition process of the present technology, leads to a significant improvement in the stability of enzyme-based biosensors. Without being limited by any theory or mechanism of action it is believed that the stabilization involves rapid protein adsorption by ion exchange, followed by the chemical interaction between aldehyde (—CHO) groups on gluteraldehyde and amino (—$NH_2$) groups on the enzyme (Zucca and Sanjust, *Methods and Mechanisms. Molecules,* 2014, 19(9): p. 14139-14194 and Ismail, I A and Wu, W. H. 1992, U.S. Pat. No. 5,116,729 A). Glutaraldehyde is advantageous as a crosslinker because of its small size (about 1 $nm^3$; Castagnola, et al., *Acta Otorhinolaryngologica Italica,* 2011, 31(6): p. 347-357) which allows its penetration into the interior of enzyme molecules. The crosslinking contributes to protein stabilization by enabling covalent, ionic, and supramolecular interactions between the protein backbone and polymer chains. It provides a simple and fast method to stabilize the adsorbed bio-reactive enzymes, while preventing them from re-folding.

An example of a layer-by-layer assembly process of making a multi-layer film to coat the working electrode is shown in FIG. 1. In this example, each layer is composed of sublayers of quaternary ammonium compound bio-linkers, metal nanoparticles, and metal nanoparticles on the surface of which a crosslinked enzyme is adsorbed. The crosslinking is performed with glutaraldehyde. For electrodes coated SWNT as sensor elements, negative charges on the SWNT interact with quaternary ammonium compounds through electrostatic attraction. Metal nanoparticles (NP) are believed to associate with the quaternary ammonium (QA) compounds and the biomolecule of choice (e.g., enzyme) through van der Waals forces or other non-covalent interactions. The QA-NP-enzyme unit layer can be repeated several times to form a multi-layered coating. The number of layers can be adjusted to achieve the best sensing performance. For example, the QA-NP-enzyme unit can be used as a single layer, or can be repeated to form from 2 to 10 layers, or from 2 to 5 layers, or from 3 to 5 layers, or from 3 to 6 layers, or from 4 to 6 layers, or from 4 to 7 layers, or from 5 to 8 layers.

Multiple identical or non-identical sensors can be included on a single chip, so that measurements can be carried out in a multiplex format or in a format that allows for internal corroboration.

The sensor element nanomaterial can be a mixture of metallic and semiconducting nanomaterials, or can be homogeneous metallic or semiconducting. The nanomaterials provide an extremely large surface-to-volume ratio and have useful electrical properties. The sensor according to the present technology operates by an electrochemical mechanism, whereby the presence of a particular analyte/biomarker results in electron transfer to the working electrode, and can be identified and quantified by measuring the resulting current flowing through the sensor. Using amperometry the current can be changed to an output voltage. This feature renders the sensor more accurate and reliable than other types of sensors that produce a change in electrical resistance of SWNT in the presence of an analyte. It is believed that with the use of biomolecules other than enzymes, which are capable of catalyzing an electron transfer reaction, conditions of detection, such as the voltage applied, can be selected such that electron transfer to or from the working electrode takes place, which can then be detected by an amperometry circuit connected to the working electrode.

The electrode material can contain or consist of, for example and without limitation, gold, platinum, iridium, silver, silver/silver chloride, copper, aluminum, chromium, or other conductive metals or other conductive material. Enzymes for use with the biosensor can be naturally occurring or recombinantly produced. Further, they can have naturally occurring or a mutant or an engineered amino acid sequence. For detection of glucose, glucose oxidase, which catalyzes an electron transfer reaction specific to glucose, may be used as the enzyme. Glucose oxidase may be isolated from a natural source, e.g. cells of *Aspergillus niger*, or produced recombinantly in transformed or transfected host cells, such as bacterial cells, yeast or fungal cells, or mammalian cells. In detection of glucose using glucose oxidase, the reaction involved is an oxidation reaction. The sensor detects levels of biomarker in the sample liquid by keeping track of the electrons passing into the working electrode and measuring the resulting current, which is detected by an amperometry detection circuit and expressed as a change in output voltage. The pathway for electrons or reaction products to reach the electrode can be by a variety of mechanisms, including diffusion, direct electron transfer from the enzyme, or a combination of mechanisms.

Sensing performance can be further improved by modifying the coated electrode with various materials, including biomolecular or porous films or membranes.

The biosensor according to the present technology may be part of a sensor system which additionally comprises a signal conditioning and/or analysis device that processes an electrical signal from the sensor. The sensor system can use either treated or untreated body fluid as a sample. Treatment of the sample fluid can be achieved, for example, by passing it through a semi-permeable membrane that coats the sensor surface. Alternatively, for ease of use, a sensor system can allow direct contact of the sensor element with a body fluid, e.g., saliva in the mouth. In one embodiment, the sensor system includes a built-in filtration mechanism, which can, for example, be a microfluidics-based system. In certain embodiments, the sensor system serves as a glucose meter that includes a signal conditioner and a microcontroller. The system can perform a series of amperometric measurements and display the glucose concentration from each measurement as an output signal or value, e.g., using a numerical display, graphic display, a dial indicator, or a color-based display indicating selected ranges or conditions. Optionally, the sensor system can compute and display an estimated equivalent blood glucose level corresponding to the measured saliva glucose level.

The above-described system can be implemented on a single chip, onto which a single drop of sample liquid is applied. The chip or sensor can be designed for single use (i.e., disposable) or for repeated use, with rinsing off or simple displacement of the sample between readings. It can be used for real-time, noninvasive monitoring of disease associated biomarkers, such as glucose, for individuals at home and around the clock. Through continuous or periodic monitoring, additional temporal information can be obtained, such as trends, magnitude, duration, and frequency of biomarker levels which allows for tracking of data for better and more accurate assessment of a disease as well as overall health condition of an individual. For example, in the case of glucose monitoring, the sensor system can activate an alarm for unusual or extreme glucose levels, thereby decreasing the nursing workload when trying to maintain tight glycemic control. Also with regards to glucose monitoring such a system can facilitate automatic feedback-controlled insulin delivery in an insulin delivery system, such as an artificial pancreas or insulin pump.

Figure 3:
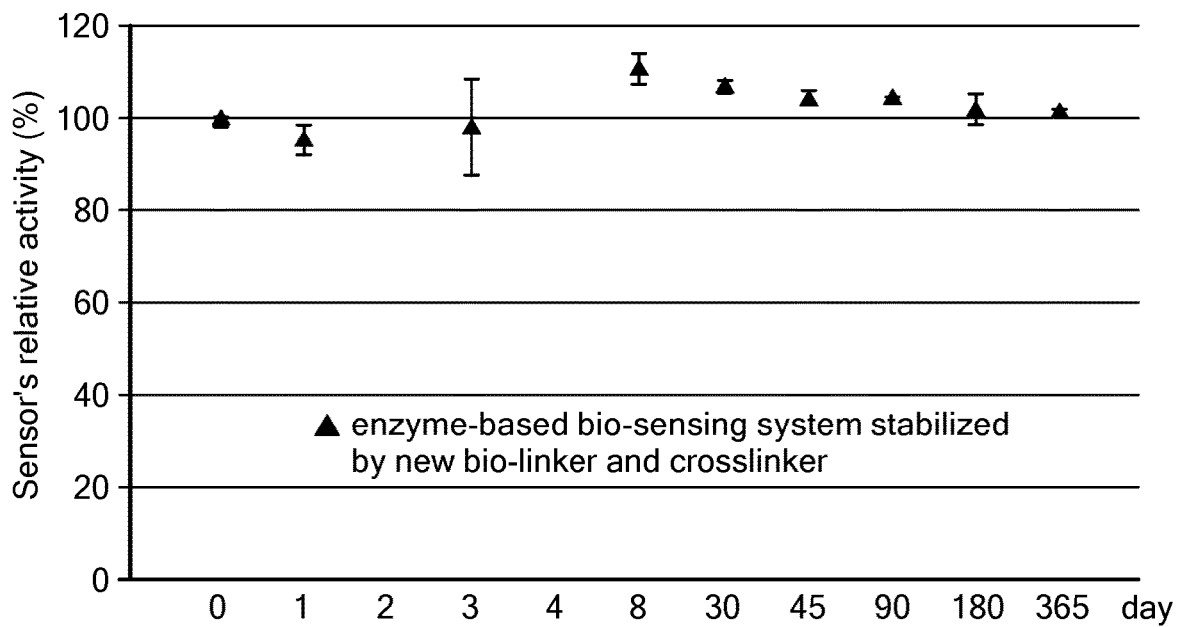
FIG. 3 shows the activity of an enzyme-based biosensor measured over the period of a year. The sensor was packed in a vacuum gel-box and stored at 4° C. Error bars: standard deviation; n=2.
Figure 4:
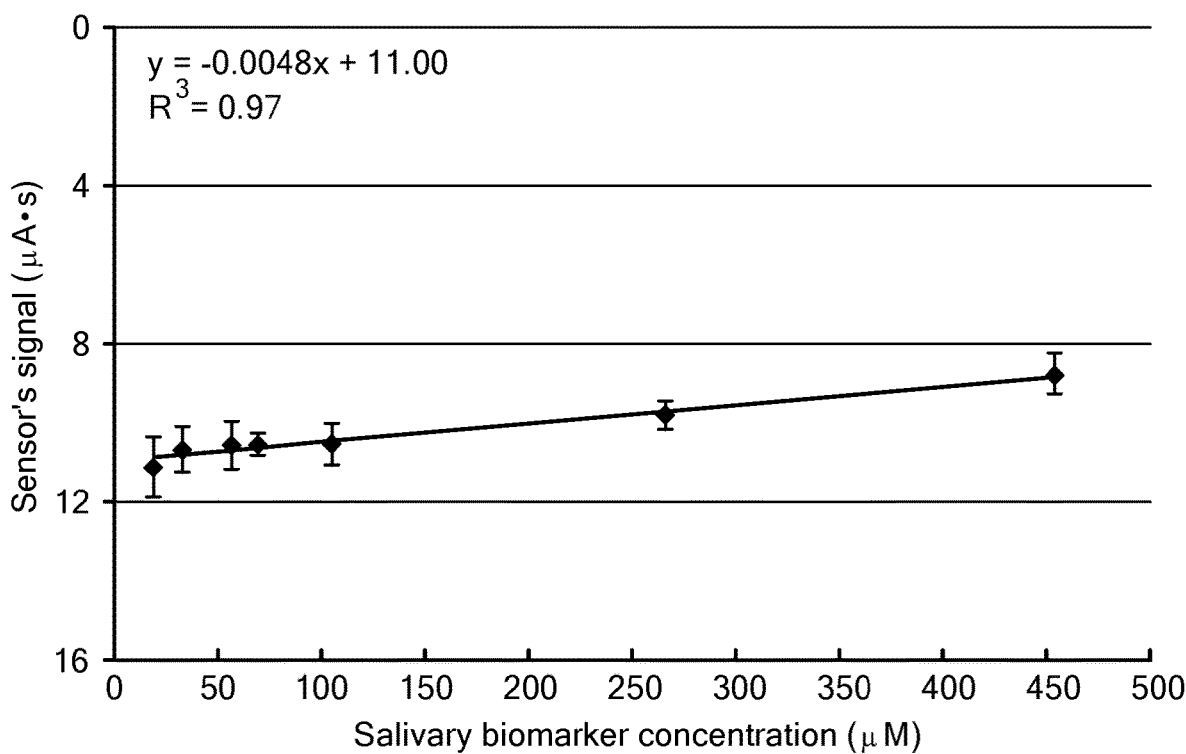
FIG. 4 depicts biomarker detection in saliva using an enzyme-based biosensor that had been in storage for 42 days at 4° C. in a vacuum gel-box. The biosensor was stabilized by use of a bio-linker and a cross-linker. Error bars: ± standard deviation and n=3.

In one embodiment of the biosensor made according to the present technology, tetrabutylammonium bromide was used as the bio-linker and glutaraldehyde crosslinked glucose oxidase as the as the enzyme for detection of glucose. The biosensor was observed to be highly accurate within the range of 5 to 500 µM, possess a good sensitivity of 4.82 mA·s/M, a low detection limit of 5 µM, and a response time of 30 seconds. See FIG. 4. The biosensor displayed a shelf life of over a year. See FIG. 3. Such durable biosensors are suitable for POC applications as well as for home use.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of."

What is claimed is:

1. A sensor for determining a concentration of a biomarker in a liquid sample, the sensor comprising:
   an insulating or semiconducting substrate;
   at least one working electrode, a counter electrode, and a reference electrode, and
   a sample placement area on a surface of the substrate for containing the liquid sample during a determination of the biomarker concentration in the liquid sample;
   wherein each of the working electrode(s), counter electrode, and reference electrode comprises a conductive metal layer deposited on the substrate in the sample placement area;
   wherein the working electrode is coated in the sample placement area with a plurality of sensor elements;
   wherein the sensor elements are functionalized with a functionalization coating comprising a quaternary ammonium compound, a plurality of metal nanoparticles, a crosslinked enzyme that catalyzes an electron transfer reaction specific for the biomarker;
   wherein the working electrode, counter electrode, and reference electrode are connected to an amperometry circuit;
   wherein the sensor measures electron transfer into the working electrode;
   wherein an output voltage of the amperometry circuit correlates with concentration of the biomarker in the liquid sample deposited in the sample placement area; and
   wherein the sensor has been fabricated by a method comprising drop deposition of the functionalization coating from a single suspension comprising the quaternary ammonium compound, the metal nanoparticles, and the enzyme.

2. The sensor of claim 1, wherein the sensor elements comprise a material selected from the group consisting of single-walled carbon nanotubes (SWNT), double-walled carbon nanotubes, multi-walled carbon nanotubes, graphite, graphene, carbon nanofibers, carbon nanowires, carbon nanorods, and combinations thereof.

3. The sensor of claim 1, wherein the functionalization coating does not contain a polycationic polymer.

4. The sensor of claim 1, wherein the quaternary ammonium compound comprises alkyl chains having a chain length from about $C_2$ to about $C_{16}$.

5. The sensor of claim 1, wherein the quaternary ammonium compound is a chloride or bromide salt.

6. The sensor of claim 1, wherein the quaternary ammonium compound is selected from the group consisting of tetraethylammonium bromide, tetrapropylammonium bromide, tetrabutylammonium bromide, hexadecyltrimethylammonium bromide, benzalkonium chloride, alkyldimethylbenzylammonium chloride having alkyl chain lengths from $C_{12}$ to $C_{16}$, and dialkyldimethylammonium chloride having alkyl chain lengths from $C_8$ to $C_{10}$.

7. The sensor of claim 1, wherein the enzyme is crosslinked using a homobifunctional or heterobifunctional crosslinking reagent.

8. The sensor of claim 1, wherein the enzyme is crosslinked by a reagent selected from the group consisting of glutaraldehyde, 1-ethyl-3-(3-dimethylaminopropyl) carbodiimide, N-hydroxysuccinimide, N-hydroxysulfosuccinimide, dicyclohexylcarbodiimide, dimethyl adipimidate, dimethyl suberimidate, and combinations thereof.

9. The sensor of claim 1, further comprising a protective membrane covering the functionalized sensor elements.

10. The sensor of claim 1 having a shelf life of at least nine months.

11. The sensor of claim 1, wherein the enzyme is glucose oxidase and the biomarker is glucose.

12. The sensor of claim 11 that is capable of detecting glucose at concentrations down to 5 µM.

13. The sensor of claim 11 that is configured for determination of glucose concentration in saliva.

14. A biomarker analysis system comprising:
the sensor of claim 1;
a signal conditioning and/or analysis device that processes an electrical signal from the sensor.

15. A biomarker sensor array comprising a plurality of sensors according to claim 1 sharing a common substrate.

16. A kit comprising the sensor of claim 1 in a vacuum storage container.

17. A method of determining a concentration of a biomarker in a liquid sample, the method comprising the steps of:
(a) providing a sensor comprising:
an insulating or semiconducting substrate;
at least one working electrode, a counter electrode, and a reference electrode, and
a sample placement area on a surface of the substrate for containing the liquid sample during a determination of the biomarker concentration in the liquid sample;
wherein each of the working electrode(s), counter electrode, and reference electrode comprises a conductive metal layer deposited on the substrate in the sample placement area;
wherein the working electrode is coated in the sample placement area with a plurality of sensor elements;
wherein the sensor elements are functionalized with a functionalization coating comprising a quaternary ammonium compound, a plurality of metal nanoparticles, a crosslinked enzyme that catalyzes an electron transfer reaction specific for the biomarker;
wherein the working electrode, counter electrode, and reference electrode are connected to an amperometry circuit;
wherein the sensor measures electron transfer into the working electrode; and
wherein an output voltage of the amperometry circuit correlates with concentration of the biomarker in the liquid sample deposited in the sample placement area;
wherein the sensor has been fabricated by a method comprising drop deposition of the functionalization coating from a single suspension comprising the quaternary ammonium compound, the metal nanoparticles, and the enzyme;
(b) introducing a liquid sample into the sample placement area of the sensor; and
(c) determining the concentration in the liquid sample from an electrical output of the sensor.

18. The method of claim 17 further comprising the steps of:
(d) removing the liquid sample introduced in step (b);
(e) introducing a new liquid sample into the sample placement area of the sensor; and
(f) determining a new biomarker concentration in the new liquid sample from an electrical output of the sensor.

19. The method of claim 17, wherein the liquid sample is saliva.

20. A method of fabricating a biomarker sensor, comprising the steps of:
(a) microfabricating one or more working electrodes, a reference electrode, and a counter electrode on the surface of an insulating substrate, wherein each of said electrodes contacts a sample placement area on the substrate;
(b) depositing a plurality of sensor elements onto the working electrode;
(c) depositing a functionalization coating onto the sensor elements, the functionalization coating comprising one or more functionalization layers; wherein each functionalization layer comprises a quaternary ammonium compound, a plurality of metal nanoparticles, an enzyme that catalyzes an electron transfer reaction specific for the biomarker, wherein the one or more functionalization layers are deposited through drop deposition of a single suspension comprising the quaternary ammonium compound, the metal nanoparticles, and the enzyme; and
(d) crosslinking the enzyme by applying a crosslinking reagent to the functionalization coating.

21. The method of claim 20, wherein the crosslinking reagent is applied to the top of the functionalization coating, or wherein the crosslinking reagent is applying by its inclusion in one or more of the one or more functionalization layers.

22. The method of claim 20, wherein the single suspension further comprises a homobifunctional or heterobifunctional crosslinking reagent.

23. The method of claim 20, wherein the sensor elements are deposited onto the working electrode by a self-assembly process comprising depositing a liquid suspension of sensor elements onto the electrode.

* * * * *